(12) United States Patent
Wu et al.

(10) Patent No.: US 10,501,529 B2
(45) Date of Patent: Dec. 10, 2019

(54) ZIKA VIRUS VACCINE COMPOSITION AND APPLICATION THEREOF

(71) Applicant: National Tsing Hua University, Hsinchu (TW)

(72) Inventors: Suh-Chin Wu, Hsinchu (TW); Shao-Ping Yang, Hsinchu (TW); Hsiao-Han Lin, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 16/037,502

(22) Filed: Jul. 17, 2018

(65) Prior Publication Data

US 2019/0248875 A1    Aug. 15, 2019

(30) Foreign Application Priority Data

Feb. 13, 2018  (TW) .............................. 107105338 A

(51) Int. Cl.

| C07K 16/10 | (2006.01) |
|---|---|
| A61K 39/12 | (2006.01) |
| C07K 14/18 | (2006.01) |
| A61K 47/68 | (2017.01) |
| A61P 31/14 | (2006.01) |
| C07K 16/00 | (2006.01) |
| A61K 39/00 | (2006.01) |
| C12N 7/00 | (2006.01) |

(52) U.S. Cl.
CPC .......... *C07K 16/1081* (2013.01); *A61K 39/12* (2013.01); *A61K 47/6839* (2017.08); *A61P 31/14* (2018.01); *C07K 14/1825* (2013.01); *A61K 2039/53* (2013.01); *C12N 7/00* (2013.01); *C12N 2770/24122* (2013.01); *C12N 2770/24134* (2013.01)

(58) Field of Classification Search
CPC ............ C07K 16/1081; C07K 14/1825; C07K 2317/56; A61K 47/6839; A61K 2039/53; A61K 39/42; C12N 2740/13022; C12N 2770/36121; C12N 15/63; Y02A 50/382; A61P 31/16; A01N 47/44
See application file for complete search history.

(56) References Cited

U.S. PATENT DOCUMENTS 10,124,055 B2 * 11/2018 Ciaramella ............ A61K 48/00

FOREIGN PATENT DOCUMENTS

WO    WO2017/109223 A1 *   6/2017

* cited by examiner

*Primary Examiner* — Bao Q Li
(74) *Attorney, Agent, or Firm* — WPAT, PC

(57) ABSTRACT

Provided herein are a mutant envelope protein of Zika virus and a nucleic acid molecule including a nucleotide sequence encoding the mutant envelope protein. The mutant envelope protein, which preferably has a threonine substitution at $105^{th}$ position, or an asparagine substitution at $248^{th}$ position and a threonine substitution at $250^{th}$ position in an amino acid sequence of SEQ ID NO: 1, includes an N-glycan masking a fusion loop region of the mutant envelope protein of Zika virus. Also provided herein is a vaccine composition, including the mutant envelope protein or a recombinant virus including the nucleic acid molecule. Also provided herein is a method of preventing Zika virus infection and reducing antibody-dependent enhancement of dengue virus infection, including administering to a subject in need thereof an effective amount of a vaccine composition including the mutant envelope protein of Zika virus.

10 Claims, 6 Drawing Sheets

Specification includes a Sequence Listing.

FIG. 2

ZIKA VIRUS VACCINE COMPOSITION AND APPLICATION THEREOF

CROSS-REFERENCE TO RELATED APPLICATION

This application claims priority of Taiwan patent application No. 107105338, filed on Feb. 13, 2018, the content of which is incorporated herein in its entirety by reference.

BACKGROUND OF THE INVENTION

1. Field of the Invention

The present invention relates to a recombinant protein, a nucleic acid molecule, and uses thereof. In particular, the present invention relates to a mutant envelope protein of Zika virus and a nucleic acid molecule comprising a corresponding nucleotide sequence thereof, a vaccine composition comprising the mutant envelope protein or a recombinant virus including the nucleic acid molecule, and a method of preventing Zika virus infection and reducing antibody-dependent enhancement of dengue virus infection using the mutant envelope protein.

2. The Prior Art

Zika virus (ZIKV) is an *Aedes* mosquito-borne virus that has raised global public health concerns since 2015 outbreak in Brazil. According to the statistics by the World Health Organization (WHO) in 2016, ZIKV had spread to over 70 countries and territories in both tropical and subtropical area in Asia, North America, Africa and Australia. Due to wide spread of the mosquito vectors, more than 2.5 million people worldwide are under risk of ZIKV infection. Symptoms of ZIKV infection are generally mild such as fever, rash, myalgia and arthralgia. However, ZIKV had been reported with neurological complications: Guillain-Barré syndrome (GBS) and neonatal microcephaly. After 2015 outbreak in Brazil, microcephaly incidents of newborn infants had increased 20 times which urged the WHO to declare a Public Health Emergency of International Concern in February 2016.

ZIKV is a member of Flaviviridae Flavivirus, which includes other mosquito-carried viruses such as dengue virus (DENV), yellow fever virus (YFV), Japanese encephalitis virus (JEV) and West Nile virus (WNV). ZIKV is a lipid-enveloped virus with around 50 nm diameter and possesses a positive-sense single-stranded RNA genome of up to 11 kb. The genome encodes a polyprotein which is post-translationally modified to form ten mature viral proteins including three structural proteins and seven non-structural proteins that correlate with viral replication. The three structural proteins are capsid protein (C), precursor membrane protein (prM), and envelope protein (E). The wild-type envelope protein has an N-glycan at amino acid residue 154, which forms anti-parallel homodimers to cover the envelope surface of Zika virus, and involves in the binding of viruses and host cell receptors and regulates the fusion of the virus envelope and the cell membrane. The envelope proteins are highly conserved and structurally similar among Flaviviridae viruses and are the main targets of host antibody responses.

More specifically, the ectodomain of the envelope protein of Zika virus consists of three domains with distinct antigenicities: domain I (DI), domain II (DII), and domain III (DIII). DII displays a finger-like structure which contains a dimerization domain and a PH-sensitive fusion loop (FL). The fusion loop is a highly conserved peptide with immunodominance that elicits weak-neutralizing antibodies that cross-react with the envelope proteins of flavivirus-like viruses. Previous studies have shown that the conserved epitope of Zika virus and DENV comprises the fusion loop and its adjacent region.

ZIKV is geographically overlapping with most of the DENV prevalence regions. Anti-Zika virus antibodies cross-react with DENV but lack the ability to neutralize DENV, and may even promote DENV to invade into cells through binding to the Fcγ receptor of leukocyte, causing antibody-dependent enhancement (ADE) and more severe symptoms of DENV infection, such as dengue hemorrhagic fever (DHF) with high lethality and dengue shock syndrome (DSS). For this reason, the study of Zika virus vaccines focuses on avoiding the aforementioned situation. In other words, there is an urgent need to develop a prophylactic Zika virus vaccine to prevent the immunization recipient from developing critical illness of DENV infection after the production of anti-Zika virus antibodies due to DENV infection through antibody-dependent enhancement.

SUMMARY OF THE INVENTION

A primary objective of the present invention is to provide a mutant envelope protein of Zika virus, comprising an N-glycan masking a fusion loop region of the mutant envelope protein of Zika virus.

According to an embodiment of the present invention, the mutant envelope protein of Zika virus has a threonine substitution at $105^{th}$ position, or an asparagine substitution at $248^{th}$ position and a threonine substitution at $250^{th}$ position in an amino acid sequence of SEQ ID NO: 1.

Another objective of the present invention is to provide a nucleic acid molecule comprising a nucleotide sequence encoding the mutant envelope protein of Zika virus, wherein the mutant envelope protein of Zika virus has a threonine substitution at $105^{th}$ position, or an asparagine substitution at $248^{th}$ position and a threonine substitution at $250^{th}$ position in an amino acid sequence of SEQ ID NO: 1.

Another objective of the present invention is to provide a vaccine composition, comprising the aforesaid mutant envelope protein of Zika virus, or a recombinant virus (e.g., a recombinant adenovirus) including the nucleic acid molecule comprising a nucleotide sequence encoding the mutant envelope protein of Zika virus.

According to an embodiment of the present invention, the vaccine composition further comprises a precursor membrane protein of Zika virus, or the recombinant virus comprises a gene encoding the precursor membrane protein of Zika virus.

Another objective of the present invention is to provide a method of preventing Zika virus infection and reducing antibody-dependent enhancement of dengue virus infection, comprising administering to a subject in need thereof an effective amount of a vaccine composition including the aforesaid mutant envelope protein of Zika virus.

According to an embodiment of the present invention, the mutant envelope protein of Zika virus is expressed by a recombinant virus, such as a recombinant adenovirus.

The mutant envelope protein of Zika virus of the present invention has additional N-glycosylation modifications due to specific point mutations. The mutant envelope protein masks the fusion loop region that is highly conserved and cross-reactive by the N-glycan, and can elicit antibodies which neutralize Zika virus but reduce antibody-dependent enhancement of dengue virus infection in a subject. Therefore, the mutant envelope protein of Zika virus of the present invention enhances the individual's immunity against Zika virus infection and at the same time reduces the risk of suffering from critical illness of dengue virus (DENV) infection in a subject. Accordingly, the mutant envelope protein of Zika virus or the recombinant virus including the nucleic acid molecule comprising the nucleotide sequence encoding the mutant envelope protein can be used to prepare the vaccine composition having the dual efficacy described above.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

FIG. 2 shows Western blot analysis of envelope proteins expressed in 293A cells infected with seven recombinant adenoviruses (i.e., AdZ-prME-wt, AdZ-prME-74, AdZ-prME-105, AdZ-prME-248, AdZ-prME-252, AdZ-prME-313, and AdZ-prME-315), including the wild-type envelope proteins without peptide-N-glycosidase F (PNGaseF) treatment or with PNGaseF treatment, and six mutant envelope proteins.

DETAILED DESCRIPTION OF THE PREFERRED EMBODIMENT

Figure 1:
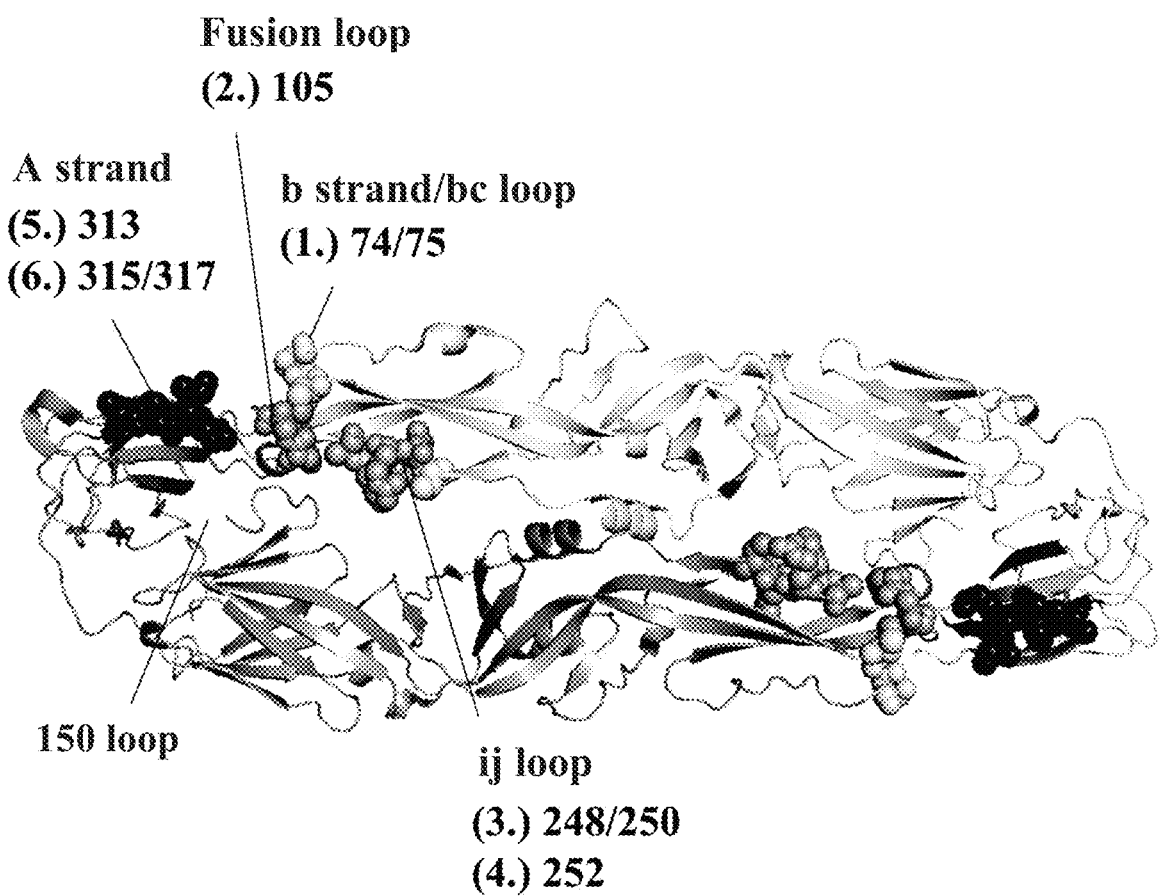
FIG. 1 is a schematic structural diagram of a dimer formed by the envelope protein of Zika virus (PDB: 5JHM), which indicates the amino acid substitution and N-glycan sites of six mutant envelope proteins in the examples of the present invention, and the 150 loop at the N154 glycans of the wild-type envelope protein.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

As used herein, the "fusion loop region" of the envelope protein of Zika virus or the mutant envelope protein thereof comprises the fusion loop of the envelope protein or the mutant envelope protein, and the region stereostructurally adjacent to the fusion loop, including the b strand, the bc loop, the ij loop, and the A strand. The fusion loop refers to the protein fragment on the amino acid residues 98 to 113, the b strand refers to the protein fragment on the amino acid residues 67 to 74, the bc loop refers to the protein fragment on the amino acid residues 75 to 89, the ij loop refers to the protein fragment on the amino acid residues 248 to 256, and the A strand refers to the protein fragment on the amino acid residues 313 to 320.

As used herein, the term "N-glycan" refers to a glycan covalently linked to the asparagine of a protein with an N-glycosidic bond, comprising about at least ten different kinds of monosaccharide units. The N-glycans have different molecular weights and structures depending on monosaccharide components.

Materials and Methods

Cell Culture

The cells used in the following examples can be purchased from the American Type Culture Collection (ATCC). The cells include human embryonic kidney cell line 293A (ATCC CRL-1573), human chronic myeloid leukemia cell line K562 (ATCC CCL-243), and Vero cells from African green monkey kidney epithelium (ATCC CCL-81) and Vero E6 cells (ATCC CRL-1586). The 293A cells were cultured in Dulbecco's Modified Essential Medium (DMEM) (Thermo Fisher Scientific) supplemented with 5% fetal bovine serum (FBS) and 100 U/ml penicillin and streptomycin (Invitrogen). The K562 cell lines were cultured in Iscove's Modified Dulbecco's Medium (IMDM) (Thermo Fisher Scientific) supplemented with 10% FBS and 100 U/ml penicillin and streptomycin. The Vero cells and the Vero E6 cells were cultured in Minimum Essential Medium (MEM) (Thermo Fisher Scientific) supplemented with 5% FBS and 100 U/ml penicillin and streptomycin. The above-mentioned cells were cultured at 37° C. and 5% $CO_2$.

Virus

ZIKV is the strain PRVABC59 (GenBank: KU501215.1); DENV2 is the strain NGC M29095. Both viruses were amplified in Vero cells. Briefly, Vero cells were infected with these viruses and cultured in MEM at 37° C. and 5% $CO_2$ for 5 days. The supernatant was collected after centrifuging the resultant cultured medium to obtain viral stocks. The viral stocks were stored at −80° C.

Sodium Dodecyl Sulfate Polyacrylamide Gel Electrophoresis (SDS-PAGE)

The samples were mixed with SDS-loading dye (50 mM Tris-HCl [pH 6.8], 2% SDS, 0.05% dithiothreitol (DTT), 0.1% bromophenol blue, and 10% glycerol) at a ratio of 3:1, and then boiled for 5 minutes. The samples were then loaded into gel which composed of 5% stacking gel (315 μL of 1 M Tris [pH 6.8], 25 μL of 10% SDS, 415 μL of 30% acrylamide mix, 1.7 mL of deionized water, 25 μL of 10% ammonium persulfate (APS), and 5 µL of TEMED) and 10% separating gel (1.25 mL of 1.0 M Tris [pH 8.8], 50 µL of 10% SDS, 1.67 mL of 30% acrylamide mix, 2 mL of deionized water, 50 µL of 10% APS, and 5 µL of TEMED). SDS-PAGE was performed in the following conditions: 80 V for the stacking step, and 120-150V for the separating step.

Western Blotting

Samples were transferred from SDS-PAGE gel to nitrocellulose (NC) membrane at 135V, and the membrane was treated with Tris(hydroxymethyl)amino buffered saline supplemented with 5% fat-free milk (abbreviated as TBST solution; 50 mM Tris, 150 mM sodium chloride, and 0.05% Tween-20), followed by shaking for at least one hour to block non-specific binding to antibodies. The membrane was washed by the TBST solution thrice, treated with anti-ZIKV envelope protein polyclonal rabbit antibodies (primary antibodies) (GeneTex) diluted 1:5000 in the TBST solution at 4° C. overnight, and washed by the TBST solution thrice. Secondary antibodies (HRP-conjugated goat anti-rabbit IgG, GeneTex) diluted 1:10000 in the TBST solution were used to detect primary antibodies, followed by washing thrice with the TBST solution. Upon detection, an enhanced chemiluminescence reagent (Western Lighting ECL; Perkin Elmer) was added to the membrane to generate a luminescence signal, and the membrane was blotted to Medical X-ray Films (Fujifilm).

Recombinant Adenovirus Titer Determination

The titer of the recombinant adenovirus was determined using the viral plaque assay to determine the amount of viral plaques that are caused by adenovirus in monolayer 293A cells. Briefly, the 293A cells were seeded in a 6-well plate at a cell density of $10^6$ cells per well. After one-day incubation at 37° C., recombinant adenovirus stocks ten-fold serially diluted with DMEM were added to each, followed by incubation at 37° C. overnight. Thereafter, the medium containing viruses was removed. Cells were overlaid with DMEM supplemented with 1% agarose (2 mL per well), cultured at 37° C. for 1-3 days, and DMEM was added again. Plaques were quantified in vision 7-10 days post-infection and were reported as plaque forming units (PFUs).

Mice Immunization and Sample Collection

BALB/c mice (6 weeks) were used in this experiment. Each mouse was intraperitoneally injected with 200 µL of phosphate buffered saline solution (abbreviated as PBS; 137 mM sodium chloride, 2.7 mM potassium chloride, 4.3 mM disodium hydrogen phosphate, 1.4 mM potassium dihydrogen phosphate, dissolved in deionized water, pH 7.4) containing $10^8$ CFU of recombinant adenovirus or PBS only. Each group of mice was given two immunizations at intervals of about three weeks. Blood samples were collected from the tail of mice two weeks after the second injection. Sera was isolated from the blood samples by centrifugation at 3000 rpm for 30 minutes, heated at 56° C. for 30 minutes to inactivate complement, and then stored at −20° C. for further analysis.

Determination of Antibody Content

The titer of immunoglobulin G (IgG) in the serum of immunized mice is determined by an enzyme-linked immunosorbent assay (ELISA). First, a binding solution (0.05 M carbonate buffer, pH 9.6) containing 0.2 µg/mL recombinant protein was added to a 96-well plate to form a recombinant protein coating. The 96-well plate was washed with the TBST solution, and blocking was performed for 1 hour at room temperature with 1% bovine serum albumin (BSA) in PBS, followed by washing with the TBST solution. Thereafter, the aforementioned serum was serially diluted by 1:40 or 1:100 with a dilution buffer containing 1% BSA and 0.05% Tween 20 in PBS for three-fold serial dilution, and added to the 96-well plate, followed by cultivation at room temperature for 1 hour. After washing with the TBST solution, the 96-well plate was incubated with HRP-conjugated goat anti-mouse IgG diluted 1:5000 at room temperature for 1 hour, followed by washing with the TBST solution. The substrate of HRP (3,3',5,5'-Tetramethyl-benzidine, TMB; Biolegend) was added to the 96-well plate. After performing color reaction for 15 minutes in the dark, the reaction was terminated with 2 N sulfuric acid. Absorbance at 450 nm ($OD_{450}$) for each well was measured using an ELISA reader. Statistically significant difference was compared via two-way ANOVA.

Plaque Reduction Neutralization Test (PRNT)

The titer of neutralizing antibodies in serum of immunized mice was determined using the plaque reduction neutralization test (PRNT). First, immunized mice sera were 2-fold diluted in a dilution ratio of 1:4 with PBS, and 100 µL of the dilution was mixed with 100 PFU of ZIKV in equal volume, followed by incubation at 37° C. for 1 hour. The mixture of the serum and virus was added to the 6-well plate seeded with Vero cells at $5 \times 10^5$ cells/well a day before, followed by incubation at 37° C. for 1 hour. Thereafter, the mixture in the 6-well plate was removed, and the decanted plate was overlaid with MEM supplemented with 1% methyl cellulose, 7.5% sodium bicarbonate, 100 U/mL penicillin-streptomycin, and 1M 2-[4-(2-hydroxyethyl) piperazin-1-yl] ethanesulfonic acid (HEPES) (2 mL/well). After 4-6 days of incubation at 37° C., the overlaid medium was removed and the cells were fixed and stained with 0.64% sodium chloride solution containing 1% crystal violet and 2% formaldehyde at room temperature for at least 1 hour, and back stained with water to quantify the viral plaque. The viral plaque amounts that are reduced by the serum-virus mixture treatment can be used to calculate the neutralization percentage of serum with different dilution multiples and to plot neutralizing curves compared to the viral plaque amounts when the cells are treated with virus alone. The titer of the neutralizing antibody is defined as the serum dilution multiple that reduces the viral plaque amounts by 50%, expressed as $PRNT_{50}$. $PRNT_{50}$ was calculated based on the neutralization test data via regression by Graph Pad Prism version 6.

Antibody-Dependent Enhancement (ADE) Assay

DENV was mixed with each immunized mice sera to infect Fcγ receptor-bearing K562 cells to determine infection enhancement Immunized mice sera or 4G2 antibodies were 4-fold serially diluted from 1:10 with IMEM, and 100 µL of the dilution was mixed with DENV2 (MOI=1) in an equal volume, followed by incubation at 37° C. for 1 hour. The mixture of the serum or the antibody and virus was added to K562 cells, followed by incubation at 37° C. for 2 hours. After washing with IMDM, the cells were seeded in a 24-well plate and incubated at 37° C. for 48 hours. Thereafter, the cells were fixed by 4% paraformaldehyde in PBS at room temperature for 30 minutes and placed at 4° C. overnight, and then treated with 0.1% Triton X-100 in PBS for 5 minutes to increase cell permeability. Cells were stained with Alexa Flour 488-labeled 4G2 antibody (1:200 in blocking buffer) for 30 minutes at room temperature, and then resuspended in PBS for flow cytometry analysis (CytoFLEX, Backmen). Fold of enhancement was compared to K562 cells that incubated with DENV2 only.

Example 1

Preparation of Recombinant Adenovirus Expressing Mutant Envelope Protein

To mask the fusion loop and its adjacent region of ZIKV that is cross-reactive, six mutant envelope proteins with an N-glycan modification in the fusion loop region were designed in this Example 1, and the N-glycosylation sites are shown in FIG. 1. Compared to the amino acid sequence of the wild-type envelope protein of ZIKV (SEQ ID NO:1), the six mutant envelope proteins have one or two amino acid substitutions to achieve N-glycosylation, including substitutions of cysteine and proline at amino acid residues 74 and 75 with asparagine and valine, substitution of cysteine at amino acid residue 105 with threonine, substitutions of two alanines at amino acid residues 248 and 250 with asparagine and threonine, substitution of arginine at amino acid residue 252 with asparagine, substitution of threonine at amino acid residue 313 with asparagine, or substitutions of threonine and isoleucine at amino acid residues 315 and 317 with asparagine and threonine (Table 1). The six mutant envelope proteins are designated $ZE_{C74NP75V}$, $ZE_{C105T}$, $ZE_{A248NA250T}$, $ZE_{R252N}$, $ZE_{T313N}$, and $ZE_{T315NI317T}$, respectively. The six mutant envelope proteins can be expressed in infected cells after infecting a host cell with the recombinant adenovirus bearing the corresponding genes, and cover the surface of replicative adenovirus.

TABLE 1

| Mutant Envelope Protein | Mutation Site | Amino Acid Sequence of N-glycosylation Site |
| --- | --- | --- |
| $ZE_{C74NP75V}$ | Residues 74 and 75 of b strand and bc loop | $^{74}NVT^{76}$ |
| $ZE_{C105T}$ | Residue 105 of fusion loop | $^{103}NGT^{105}$ |
| $ZE_{A248NA250T}$ | Residues 248 and 250 of ij loop | $^{248}NHT^{250}$ |
| $ZE_{R252N}$ | Residue 252 of ij loop | $^{252}NQT^{254}$ |
| $ZE_{T313N}$ | Residue 313 of A strand | $^{313}NFT^{315}$ |
| $ZE_{T315NI317T}$ | Residues 315 and 317 of A strand | $^{315}NKT^{317}$ |

To construct an adenoviral expression vector comprising the gene encoding the mutant envelope protein, a codon-optimized DNA was prepared in a synthetic manner, including a DNA fragment encoding the C protein terminal signal peptide (SEQ ID NO:2), a gene encoding the precursor membrane protein of the wild-type ZIKV (SEQ ID NO:3), and a gene encoding the envelope protein of the wild-type ZIKV (SEQ ID NO:4) from 5' end to 3' end. The DNA and the primers listed in Table 2 were subjected to site-directed mutagenesis using polymerase chain reaction (PCR) to obtain the DNA comprising the gene encoding the mutant envelope protein. The sequence of the DNA comprising the gene encoding the mutant envelope protein was confirmed by DNA sequencing, and the DNA was cloned into entry vector pENTR1A (Invitrogen) via KpnI and XhoI restriction sites, followed by cloning into adenoviral expression vector pAd/CMV/V5-DEST (Thermo Fisher Scientific) by way of LR Clonase II Enzyme Mix.

TABLE 2

| Mutant Envelope Protein | Sequence of Forward Primer (F) and Reverse Primer (R) |
| --- | --- |
| $ZE_{C74NP75V}$ | F: GATAGCAGAAATGTCACCCAGGG (SEQ ID NO: 5)<br>R: CCCTGGGTGACATTTCTGCTATC (SEQ ID NO: 6) |
| $ZE_{C105T}$ | F: GGCAATGGCACTGGCCTGTTT (SEQ ID NO: 7)<br>R: AAACAGGCCAGTGCCATTGCC (SEQ ID NO: 8) |
| $ZE_{A248NA250T}$ | F: TTCAAGGATAACCACACCAAGAG (SEQ ID NO: 9)<br>R: CTCTTGGTGTGGTTATCCTTGAA (SEQ ID NO: 10) |
| $ZE_{R252N}$ | F: CACGCCAAGAACCAGACAGTG (SEQ ID NO: 11)<br>R: CACTGTCTGGTTCTTGGCGTG (SEQ ID NO: 12) |
| $ZE_{T313N}$ | F: GCCGCCTTCAACTTCACCAAG (SEQ ID NO: 13)<br>R: CTTGGTGAAGTTGAAGGCGGC (SEQ ID NO: 14) |
| $ZE_{T315NI317T}$ | F: TTCACCTTCAACAAGACCCCTG (SEQ ID NO: 15)<br>R: CAGGGGTCTTGTTGAAGGTGAA (SEQ ID NO: 16) |

To obtain recombinant adenoviral particles that can be used to prepare vaccines, the aforementioned adenoviral expression vector was transfected into 293A cells by Turbofect reagent (Fermentas) after exposing inverted terminal repeats (ITRs) by digestion of restriction enzyme PacI. After the transfected cells were cultured at 37° C. for 11-14 days until 95% cells detached with cytopathic effect, the cells and the medium were collected. The cell lysates thus obtained were freezed and thawed from −80 to 37° C. for 3 rounds to destroy cells and release intracellular viral particles. The supernatant of the cell lysates was collected by centrifugation (3000 rpm, 10 minutes, 4° C.) to obtain stocks of the recombinant adenovirus, and the stocks were stored at −80° C. The recombinant adenoviruses that can be used to express the precursor membrane protein of ZIKV (comprising the amino acid sequence of SEQ ID NO:17) and the mutant envelope proteins $ZE_{C74NP75V}$, $ZE_{C105T}$, $ZE_{A248NA250T}$, $ZE_{R252N}$, $ZE_{T313N}$, or $ZE_{T315NI317T}$ are designated as AdZ-prME-74, AdZ-prME-105, AdZ-prME-248, AdZ-prME-252, AdZ-prME-313, and AdZ-prME-315, respectively. As a control, the recombinant adenovirus that can be used to express the precursor membrane protein and the envelope protein of the wild-type ZIKV is designated as AdZ-prME-wt.

Figure 2:
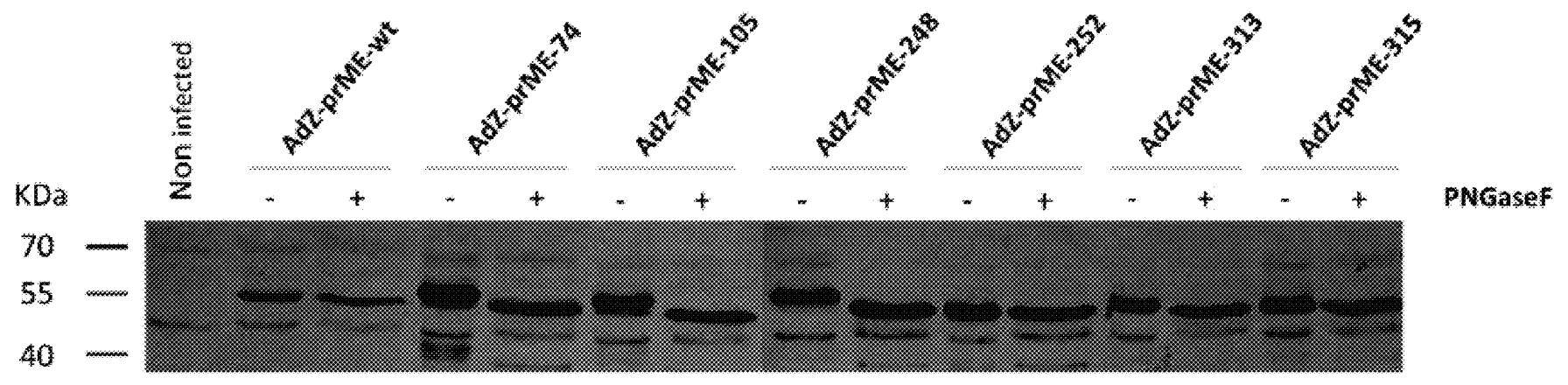

Western blotting was performed to confirm whether human cells can express the mutant envelope protein with an N-glycan after infected with the aforementioned recombinant adenovirus. $10^6$ 293A cells were seeded in a 6-well plate. After one day of incubation, the cells were infected with the aforementioned recombinant adenovirus at multiplicity of infection (MOI) of 2 for 24 hours. Thereafter, the infected cells were treated with Glo lysis buffer (Promega) for 5 minutes, and the supernatant of the cell lysates was collected by centrifugation (10000×g, 20 minutes, 4° C.). To examine the presence of the N-glycan on the mutant envelope protein, the supernatant was boiled and treated with PNGaseF (NEB) at 37° C. for 1-2 hours, followed by SDS-PAGE and Western blotting analysis. As shown in FIG. 2, without PNGaseF treatment, the wild-type envelope protein or the mutant envelope protein expressed by cells infected with the recombinant adenovirus can be detected using anti-ZIKV envelope protein antibodies. The molecular weight is around 54 kDa. When PNGaseF was used to remove N-glycans, the wild-type envelope protein was detected at slightly below 54 kDa due to the removal of N154 glycans. In contrast, obvious band shift was observed in the groups of AdZ-prME-74, AdZ-prME-105, AdZ-prME-248, and AdZ-prME-313, demonstrating the existence of extra N-glycans on the mutant envelope proteins $ZE_{C74NP75V}$, $ZE_{C105T}$, $ZE_{A248N4250T}$, and $ZE_{T313N}$ due to mutations. However, slight band shift was observed in the groups of AdZ-prME-252 and AdZ-prME-315, indicating low level of extra N-glycans on the mutant envelope proteins $ZE_{R252N}$ and $ZE_{T315N1317T}$.

Example 2

Immune Injection of Recombinant Adenovirus Elicits Antigen-Specific IgG

To examine the immune effect regarding the mutant envelope protein of ZIKV of the present invention, two doses of PBS (negative control group) or the recombinant adenovirus ($10^8$ PFU/200 µL) in Example 1 were administered to BALB/c mice (4-5 mice in each group) by intraperitoneal injection, and the total IgG titers of domain III (ZDIII) of the envelope protein of ZIKV in serum of the mice were detected using enzyme-linked immunosorbent assay (ELISA). The interval of two immune injections is about three weeks, and blood samples of the mice were collected two weeks after the second injection. The endpoint titer of the total IgG is the serum dilution multiple that results in an $OD_{450}$ value of 0.2 in the ELISA experiment.

Figure 3:
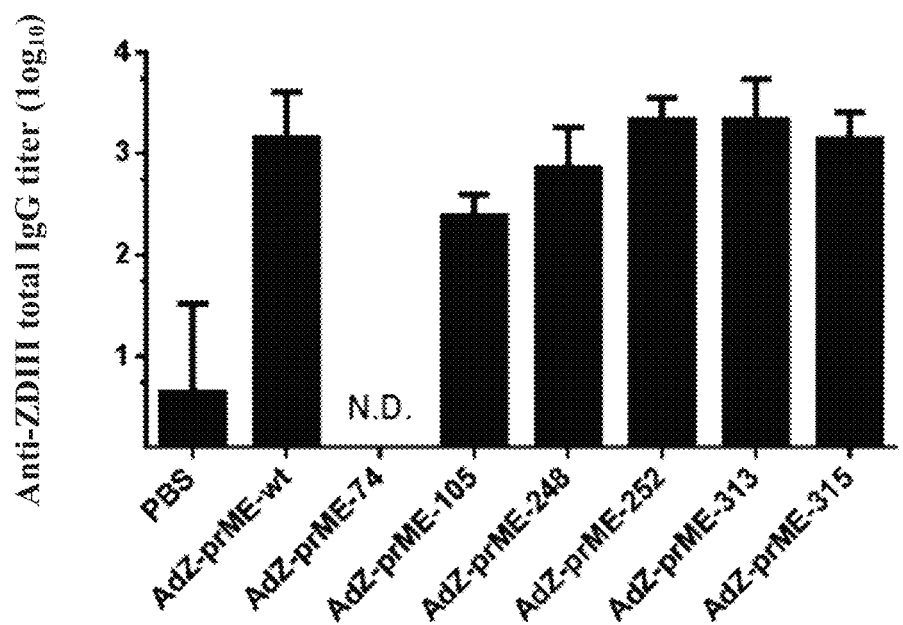
FIG. 3 shows the titer of total immunoglobulin G (IgG) against domain III (ZDIII) of the envelope protein of the recombinant Zika virus in serum of BALB/c mice after various immunizations; the immunization was administered with phosphate buffered saline (PBS) solution, AdZ-prME-wt, AdZ-prME-74, AdZ-prME-105, AdZ-prME-248, AdZ-prME-252, AdZ-prME-313, or AdZ-prME-315.

FIG. 3 shows the titer of total IgG against ZDIII of the recombinant protein in sera of immunized mice, in which N.D. indicates no detection. According to FIG. 3, injections of the recombinant adenovirus AdZ-prME-wt can elicit anti-ZDIII IgG with the titer of approximately 1980, and injections of AdZ-prME-252, AdZ-prME-313, or AdZ-prME-315 can also elicit high titer of anti-ZDIII IgG; injections of AdZ-prME-105 or AdZ-prME-248 can elicit less amount of anti-ZDIII IgG (titer approximately 260-1020), but no significant differences with the group of AdZ-prME-wt. In contrast, immune injections of AdZ-prME-74 failed to elicit anti-ZDIII IgG This result shows that in addition to the mutant envelope protein $ZE_{C74NP75V}$, the mutant envelope protein of ZIKV of the present invention, in which the fusion loop region is masked by N-glycans, can elicit antigen-specific IgG in a subject.

Example 3

Immune Injection of Recombinant Adenovirus Elicits Neutralizing Antibodies Against ZIKV In the present example, after different immune injections according to the method described in Example 2, the titer of neutralizing antibodies against ZIKV in sera of immunized mice was determined using the plaque reduction neutralization test (PRNT). During the experiment, ten-fold diluted immunized sera or its two-fold serial dilutions were mixed and incubated with 100 PFU of ZIKV. Vero cells were then infected with the mixture of sera and virus to calculate the amount of viral plaques and to obtain the neutralizing curves. The titer of the neutralizing antibody is defined as the serum dilution multiple that reduces the viral plaque amounts by 50%, expressed as $PRNT_{50}$.

Figure 4A:
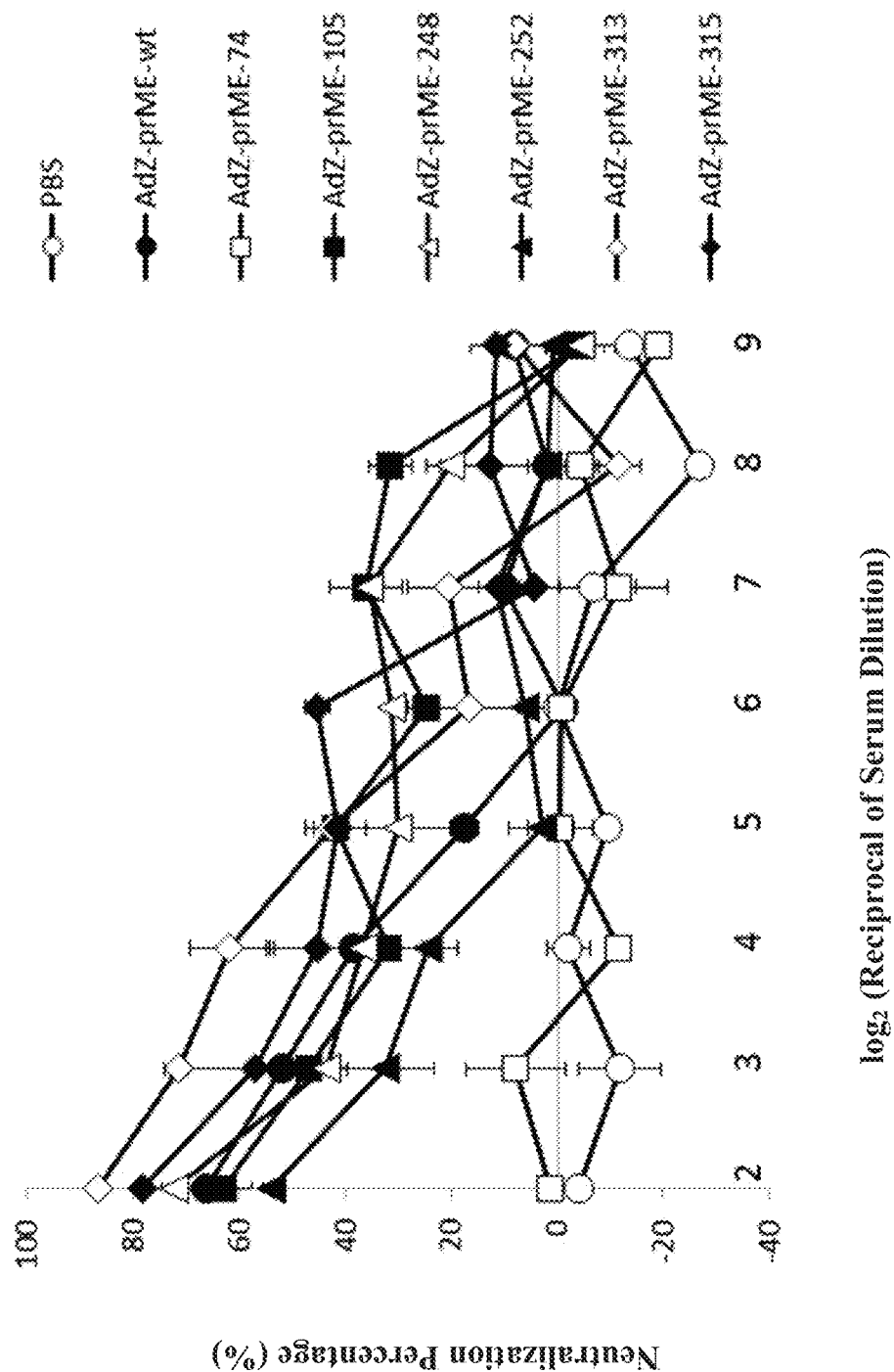
FIG. 4A shows neutralizing curves of neutralizing antibodies against Zika virus in serum of BALB/c mice after various immunizations; the immunization was administered with PBS, AdZ-prME-wt, AdZ-prME-74, AdZ-prME-105, AdZ-prME-248, AdZ-prME-252, AdZ-prME-313, or AdZ-prME-315.
Figure 4B:
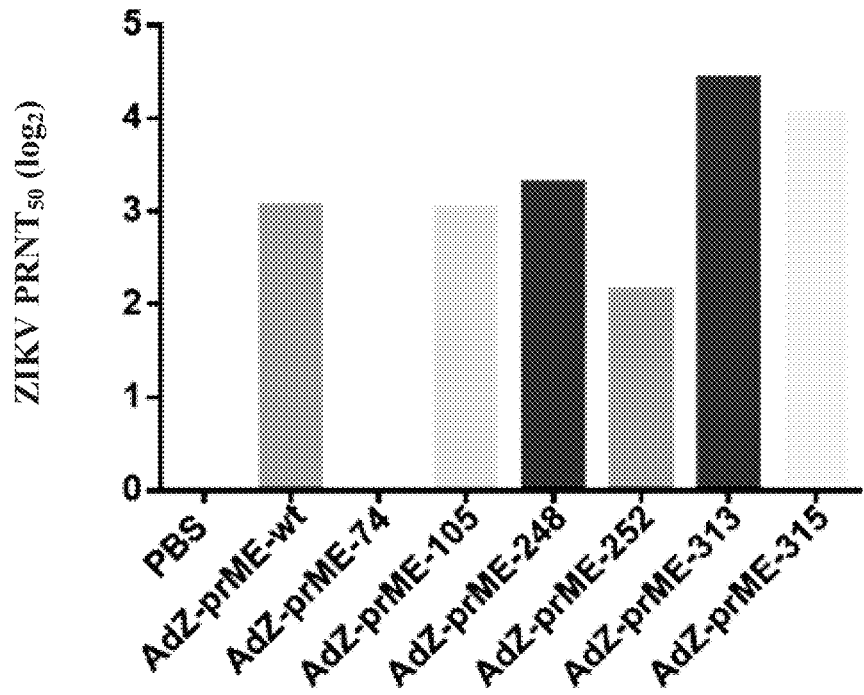
FIG. 4B calculates the titer of neutralizing antibodies against Zika virus in serum of BALB/c mice after various immunizations according to FIG. 4A; the immunization was administered with PBS, AdZ-prME-wt, AdZ-prME-74, AdZ-prME-105, AdZ-prME-248, AdZ-prME-252, AdZ-prME-313, or AdZ-prME-315.

FIG. 4A shows neutralizing curves of neutralizing antibodies against ZIKV in serum of immunized mice; FIG. 4B shows the titer of neutralizing antibodies calculated from FIG. 4A. According to FIG. 4A, PBS or the immunized sera of AdZ-prME-74 failed to neutralize ZIKV at any dilution multiple. In contrast, the immunized sera of AdZ-prME-wt neutralized the virus up to 65% at a ten-fold dilution, and its viral neutralizing capacity decreased as the dilution multiple increased. Similarly, the immunized sera of AdZ-prME-105, AdZ-prME-248, AdZ-prME-252, AdZ-prME-313, or AdZ-prME-315 neutralized the virus up to 55-85% at a ten-fold dilution, and can neutralize the virus in a dose-dependent manner. According to FIG. 4B, the titer of neutralizing antibodies elicited by AdZ-prME-wt, AdZ-prME-105, or AdZ-prME-248 is approximately 10, the titer of neutralizing antibodies elicited by AdZ-prME-252 is approximately 5, and the titer of neutralizing antibodies elicited by AdZ-prME-313 or AdZ-prME-315 is approximately 20. These results show that in addition to the mutant envelope protein $ZE_{C74NP75V}$, the mutant envelope protein of ZIKV of the present invention, in which the fusion loop region is masked by N-glycans, can elicit neutralizing antibodies against ZIKV in a subject.

Example 4

Immunized Sera of Recombinant Adenovirus Reduces Enhancement of DENV Infection

In the present example, after different immune injections according to the method described in Example 2, the antibody-dependent enhancement (ADE) assay was used to determine whether the immunized sera of mice reduce antibody-dependent enhancement of DENV infection. During the experiment, ten-fold diluted immunized sera or its two-fold serial dilutions were mixed and incubated with DENV2. Lymphoblast cells K562 were then infected with the mixture of sera and virus to measure the fold of infection enhancement. The fold of infection enhancement was compared with the degree of infection of K562 cells that only incubated with viruses. 4G2 antibodies against the envelope protein of Flavivirus were used as the positive control for the ADE assay of DENV, and the antibodies have been demonstrated to recognize envelope proteins of DENV and ZIKV.

Figure 5:
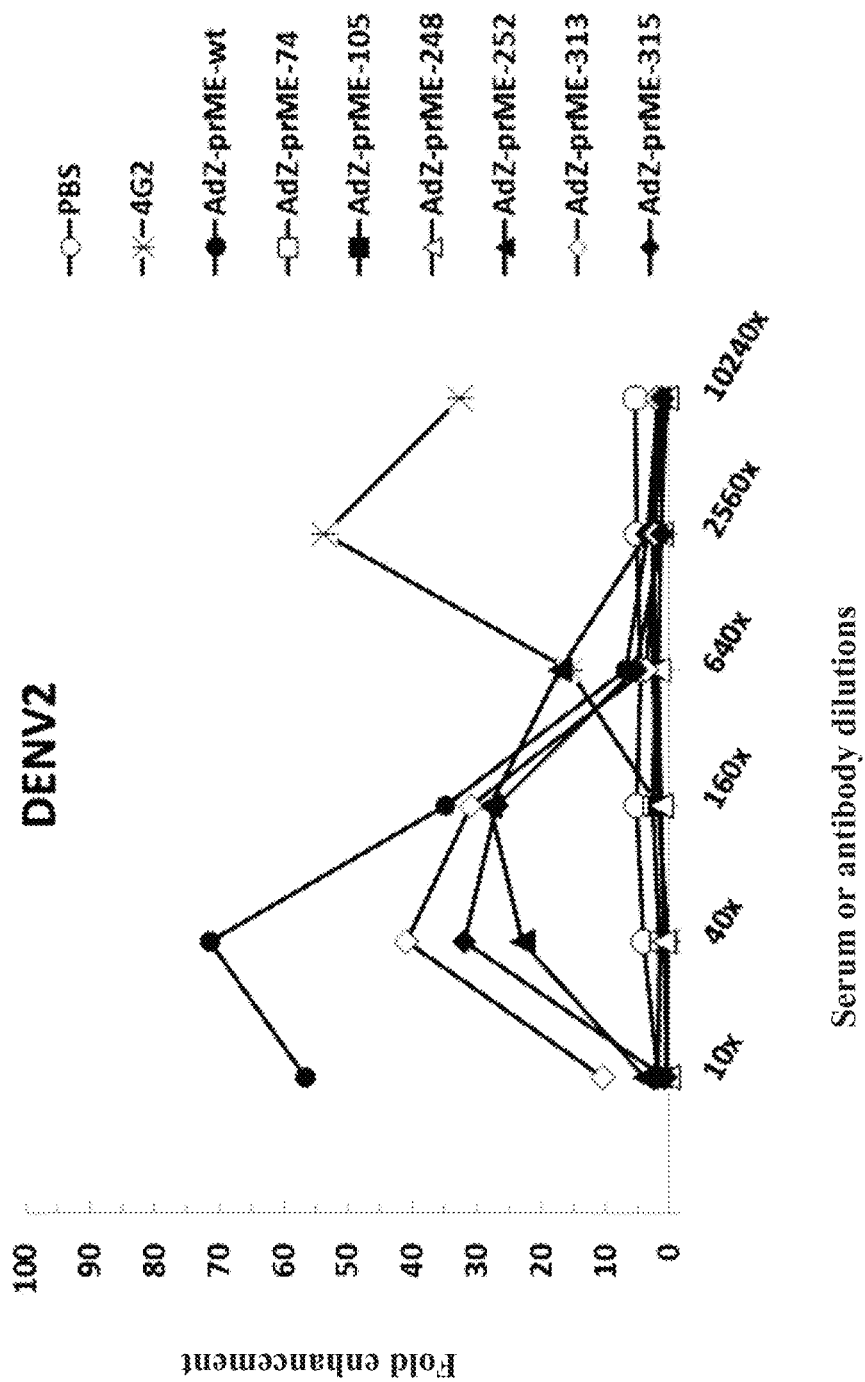
FIG. 5 shows DENV type 2 (DENV2) infection enhancement with serum of BALB/c mice after various immunizations in K562 cells; the immunization was administered with PBS, AdZ-prME-wt, AdZ-prME-74, AdZ-prME-105, AdZ-prME-248, AdZ-prME-252, AdZ-prME-313, or AdZ-prME-315.

FIG. 5 shows the enhancement effect of sera in immunized mice on DENV2-infected K562 cells. According to FIG. 5, PBS failed to enhance infection at any dilution multiple, but 4G2 antibodies enhanced infection from 640-fold to 10240-fold dilution, especially as 60-fold infection enhancement at 2560-fold dilution. Robust enhancement was observed in immunized sera of AdZ-prME-wt at 10-, 40-, and 160-fold dilution with respectively up to 65-, 80- and 40-fold enhancement, supporting cross-reactive immunity between anti-ZIKV and anti-DENV antibodies in serum, thus promoting DENV infection. In contrast, the immunized sera of AdZ-prME-105 or AdZ-prME-248 did not enhance the infection, and the curves of the two groups almost overlapped with the PBS group. Although the immunized sera of AdZ-prME-252, AdZ-prME-313, or AdZ-prME-315 enhanced the infection, the 10-fold and 40-fold dilutions thereof showed significantly lower enhancement than that of the AdZ-prME-wt group. This result indicates that the antibody elicited by the mutant envelope protein of ZIKV in which the fusion loop region is masked by N-glycans has poor cross reaction with DENV, and thus can reduce or even avoid antibody-dependent enhancement of DENV infection. For example, $ZE_{C105T}$ and $ZE_{A248N4250T}$ mutants can elicit antibodies that completely prevent enhancement of DENV infection.

In summary, the mutant envelope protein of ZIKV of the present invention has additional N-glycosylation modifications due to specific point mutations. In contrast to antibodies elicited by the wild-type envelope protein that neutralize ZIKV but significantly enhance DENV infection, the mutant envelope protein masks the fusion loop region that is highly conserved and cross-reactive by the N-glycan, and can elicit antibodies which neutralize ZIKV but reduce antibody-dependent enhancement of DENV infection in a subject. Therefore, the mutant envelope protein of ZIKV of the present invention enhances the individual's immunity against ZIKV infection and at the same time reduces the risk of suffering from critical illness of DENV infection in a subject. Accordingly, the mutant envelope protein of ZIKV, particularly the mutant envelope protein comprising single substitution of C105T or double substitutions of A248N and A250T, or a recombinant virus including the nucleic acid molecule comprising the nucleotide sequence encoding the mutant envelope protein can be used to prepare the vaccine composition having the dual efficacy described above.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A mutant envelope protein of Zika virus, comprising an N-glycan masking a fusion loop region of the mutant envelope protein of Zika virus, wherein the mutant envelope protein of Zika virus has an asparagine substitution at 248$^{th}$ position and a threonine substitution at 250$^{th}$ position in an amino acid sequence of SEQ ID NO: 1.

2. A nucleic acid molecule, comprising a nucleotide sequence encoding the mutant envelope protein of Zika virus according to claim 1.

3. A vaccine composition, comprising the mutant envelope protein of Zika virus according to claim 1.

4. The vaccine composition according to claim 3, further comprising a precursor membrane protein of Zika virus.

5. A vaccine composition, comprising a recombinant virus including the nucleic acid molecule according to claim 2.

6. The vaccine composition according to claim 5, wherein the recombinant virus comprises a gene encoding a precursor membrane protein of Zika virus.

7. The vaccine composition according to claim 5, wherein the recombinant virus is a recombinant adenovirus.

8. A method of preventing Zika virus infection and reducing antibody-dependent enhancement of dengue virus infection, comprising administering to a subject in need thereof an effective amount of a vaccine composition including a mutant envelope protein of Zika virus, wherein the mutant envelope protein of Zika virus comprises an N-glycan masking a fusion loop region of the mutant envelope protein of Zika virus, wherein the mutant envelope protein of Zika virus has an asparagine substitution at 248$^{th}$ position and a threonine substitution at 250$^{th}$ position in an amino acid sequence of SEQ ID NO: 1.

9. The method according to claim 8, wherein the mutant envelope protein of Zika virus is expressed by a recombinant virus.

10. The method according to claim 9, wherein the recombinant virus is a recombinant adenovirus.

* * * * *

SEQUENCE LISTING

```
<160> NUMBER OF SEQ ID NOS: 17

<210> SEQ ID NO 1
<211> LENGTH: 504
<212> TYPE: PRT
<213> ORGANISM: Zika virus

<400> SEQUENCE: 1

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285
```

```
Leu Lys Cys Arg Leu Lys Met Asp Lys Leu Arg Leu Lys Gly Val Ser
    290                 295                 300
Tyr Ser Leu Cys Thr Ala Ala Phe Thr Phe Thr Lys Ile Pro Ala Glu
305                 310                 315                 320
Thr Leu His Gly Thr Val Thr Val Glu Val Gln Tyr Ala Gly Thr Asp
                325                 330                 335
Gly Pro Cys Lys Val Pro Ala Gln Met Ala Val Asp Met Gln Thr Leu
            340                 345                 350
Thr Pro Val Gly Arg Leu Ile Thr Ala Asn Pro Val Ile Thr Glu Ser
        355                 360                 365
Thr Glu Asn Ser Lys Met Met Leu Glu Leu Asp Pro Pro Phe Gly Asp
    370                 375                 380
Ser Tyr Ile Val Ile Gly Val Gly Glu Lys Lys Ile Thr His His Trp
385                 390                 395                 400
His Arg Ser Gly Ser Thr Ile Gly Lys Ala Phe Glu Ala Thr Val Arg
                405                 410                 415
Gly Ala Lys Arg Met Ala Val Leu Gly Asp Thr Ala Trp Asp Phe Gly
            420                 425                 430
Ser Val Gly Gly Ala Leu Asn Ser Leu Gly Lys Gly Ile His Gln Ile
        435                 440                 445
Phe Gly Ala Ala Phe Lys Ser Leu Phe Gly Gly Met Ser Trp Phe Ser
    450                 455                 460
Gln Ile Leu Ile Gly Thr Leu Leu Met Trp Leu Gly Leu Asn Thr Lys
465                 470                 475                 480
Asn Gly Ser Ile Ser Leu Met Cys Leu Ala Leu Gly Gly Val Leu Ile
                485                 490                 495
Phe Leu Ser Thr Ala Val Ser Ala
            500

<210> SEQ ID NO 2
<211> LENGTH: 60
<212> TYPE: DNA
<213> ORGANISM: Artificial sequence
<220> FEATURE:
<223> OTHER INFORMATION: C protein terminal signal peptide

<400> SEQUENCE: 2
cggagaggag cagacacaag cgtgggaatc gtgggactgc tgctgaccac agcaatggca    60

<210> SEQ ID NO 3
<211> LENGTH: 504
<212> TYPE: DNA
<213> ORGANISM: Zika virus

<400> SEQUENCE: 3
gcagaggtga ccaggagggg atctgcctac tatatgtacc tggaccggaa tgatgccggc    60
gaggccatca gctttcccac cacactgggc atgaacaagt gctacatcca gatcatggac   120
ctgggccaca tgtgcgatgc caccatgtcc tatgagtgtc caatgctgga cgagggcgtg   180
gagcccgacg atgtggattg ctggtgtaac accacatcca catgggtggt gtacggcacc   240
tgtcaccaca agaagggaga ggcacggaga tctaggaggg cagtgacact gccttcccac   300
tctacccgga agctgcagac aagatctcag acctggctgg agagcagaga gtataccaag   360
cacctgatcc gggtggagaa ctggatcttt agaaatccag gattcgcact ggcagcagca   420
gcaatcgcct ggctgctggg cagctccacc tctcagaaag tgatctacct ggtcatgatc   480
ctgctgatcg ccccctgccta ttcc                                         504
```

<210> SEQ ID NO 4
<211> LENGTH: 1512
<212> TYPE: DNA
<213> ORGANISM: Zika virus

<400> SEQUENCE: 4

```
atcaggtgca tcggcgtgtc taatagggac ttcgtggagg gaatgagcgg aggaacctgg      60
gtggatgtgg tgctggagca cggcggctgc gtgacagtga tggcccagga caagccaacc     120
gtggatatcg agctggtgac cacaaccgtg agcaacatgg ccgaggtgcg gtcctactgc     180
tatgaggcca gcatctccga catggcctct gatagcagat gtcccaccca gggcgaggcc     240
tacctggaca gcagagcga tacacagtac gtgtgcaaga ggaccctggt ggatcgcggc     300
tggggcaatg gctgtggcct gtttggcaag ggctccctgg tgacatgcgc caagttcgcc     360
tgttctaaga gatgaccgg caagagcatc cagccagaga acctggagta caggatcatg     420
ctgtccgtgc acggctccca gcactctggc atgatcgtga cgacacagg ccacgagacc     480
gatgagaata gggccaaggt ggagatcaca cctaacagcc aagggcaga ggccacccctg    540
ggaggatttg gatccctggg actggactgc gagcctagga caggcctgga cttctctgat     600
ctgtactatc tgaccatgaa caataagcac tggctggtgc acaaggagtg gtttcacgac     660
atcccactgc catggcacgc aggagcagat acaggaaccc cacactggaa caataaggag     720
gccctggtgg agttcaagga tgcccacgcc aagaggcaga cagtggtggt gctgggcagc     780
caggagggag cagtgcacac cgcccctggca ggcgccctgg aggccgagat ggacggagca     840
aagggccgcc tgtctagcgg ccacctgaag tgccggctga agatggataa gctgagactg     900
aagggcgtgt cctactctct gtgcacagcc gccttcacct tcaccaagat ccctgccgag     960
accctgcacg gcacagtgac cgtggaggtg cagtatgccg gcacagacgg cccctgtaag    1020
gtgcctgccc agatggccgt ggatatgcag acactgaccc ctgtgggccg gctgatcacc    1080
gcaaatccag tgatcacaga gtctaccgag aacagcaaga tgatgctgga gctggacccc    1140
cctttcggcg atagctacat cgtgatcggc gtgggcgaga agaagatcac acaccactgg    1200
cacagaagcg gctccacaat cggcaaggcc tttgaggcaa ccgtgcgggg agcaaagaga    1260
atggccgtgc tgggcgacac cgcatgggat ttcggatccg tgggaggcgc cctgaattct    1320
ctgggcaagg gcatccacca gatcttcggc gccgccttta gtccctgtt cggcggcatg    1380
agctggtttt cccagatcct gatcggcaca ctgctgatgt ggctgggcct gaacaccaag    1440
aatggctcta tcagcctgat gtgcctggcc ctggaggcg tgctgatctt cctgtccacc    1500
gccgtgtctg cc                                                        1512
```

<210> SEQ ID NO 5
<211> LENGTH: 23
<212> TYPE: DNA
<213> ORGANISM: Artificial sequence
<220> FEATURE:
<223> OTHER INFORMATION: PCR primer for site-directed mutagenesis

<400> SEQUENCE: 5

```
gatagcagaa atgtcaccca ggg                                               23
```

<210> SEQ ID NO 6
<211> LENGTH: 23
<212> TYPE: DNA
<213> ORGANISM: Artificial sequence
<220> FEATURE:

```
<223> OTHER INFORMATION: PCR primer for site-directed mutagenesis

<400> SEQUENCE: 6
ccctgggtga catttctgct atc                                             23

<210> SEQ ID NO 7
<211> LENGTH: 21
<212> TYPE: DNA
<213> ORGANISM: Artificial sequence
<220> FEATURE:
<223> OTHER INFORMATION: PCR primer for site-directed mutagenesis

<400> SEQUENCE: 7
ggcaatggca ctggcctgtt t                                               21

<210> SEQ ID NO 8
<211> LENGTH: 21
<212> TYPE: DNA
<213> ORGANISM: Artificial sequence
<220> FEATURE:
<223> OTHER INFORMATION: PCR primer for site-directed mutagenesis

<400> SEQUENCE: 8
aaacaggcca gtgccattgc c                                               21

<210> SEQ ID NO 9
<211> LENGTH: 23
<212> TYPE: DNA
<213> ORGANISM: Artificial sequence
<220> FEATURE:
<223> OTHER INFORMATION: PCR primer for site-directed mutagenesis

<400> SEQUENCE: 9
ttcaaggata accacaccaa gag                                             23

<210> SEQ ID NO 10
<211> LENGTH: 23
<212> TYPE: DNA
<213> ORGANISM: Artificial sequence
<220> FEATURE:
<223> OTHER INFORMATION: PCR primer for site-directed mutagenesis

<400> SEQUENCE: 10
ctcttggtgt ggttatcctt gaa                                             23

<210> SEQ ID NO 11
<211> LENGTH: 21
<212> TYPE: DNA
<213> ORGANISM: Artificial sequence
<220> FEATURE:
<223> OTHER INFORMATION: PCR primer for site-directed mutagenesis

<400> SEQUENCE: 11
cacgccaaga accagacagt g                                               21

<210> SEQ ID NO 12
<211> LENGTH: 21
<212> TYPE: DNA
<213> ORGANISM: Artificial sequence
<220> FEATURE:
<223> OTHER INFORMATION: PCR primer for site-directed mutagenesis

<400> SEQUENCE: 12
cactgtctgg ttcttggcgt g                                               21
```

-continued

<210> SEQ ID NO 13
<211> LENGTH: 21
<212> TYPE: DNA
<213> ORGANISM: Artificial sequence
<220> FEATURE:
<223> OTHER INFORMATION: PCR primer for site-directed mutagenesis

<400> SEQUENCE: 13
gccgccttca acttcaccaa g 21

<210> SEQ ID NO 14
<211> LENGTH: 21
<212> TYPE: DNA
<213> ORGANISM: Artificial sequence
<220> FEATURE:
<223> OTHER INFORMATION: PCR primer for site-directed mutagenesis

<400> SEQUENCE: 14
cttggtgaag ttgaaggcgg c 21

<210> SEQ ID NO 15
<211> LENGTH: 22
<212> TYPE: DNA
<213> ORGANISM: Artificial sequence
<220> FEATURE:
<223> OTHER INFORMATION: PCR primer for site-directed mutagenesis

<400> SEQUENCE: 15
ttcaccttca acaagacccc tg 22

<210> SEQ ID NO 16
<211> LENGTH: 22
<212> TYPE: DNA
<213> ORGANISM: Artificial sequence
<220> FEATURE:
<223> OTHER INFORMATION: PCR primer for site-directed mutagenesis

<400> SEQUENCE: 16
caggggtctt gttgaaggtg aa 22

<210> SEQ ID NO 17
<211> LENGTH: 168
<212> TYPE: PRT
<213> ORGANISM: Zika virus

<400> SEQUENCE: 17

```
Ala Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Arg Val Glu Asn Trp
        115                 120                 125
```

-continued

```
Ile Phe Arg Asn Pro Gly Phe Ala Leu Ala Ala Ala Ile Ala Trp
    130             135                 140

Leu Leu Gly Ser Ser Thr Ser Gln Lys Val Ile Tyr Leu Val Met Ile
145             150                 155                 160

Leu Leu Ile Ala Pro Ala Tyr Ser
                165
```